March 5, 1974 J. DESMARTIS Plant Pat. 3,504
LAGERSTROEMIA INDICIA PLANT
Filed May 22, 1972
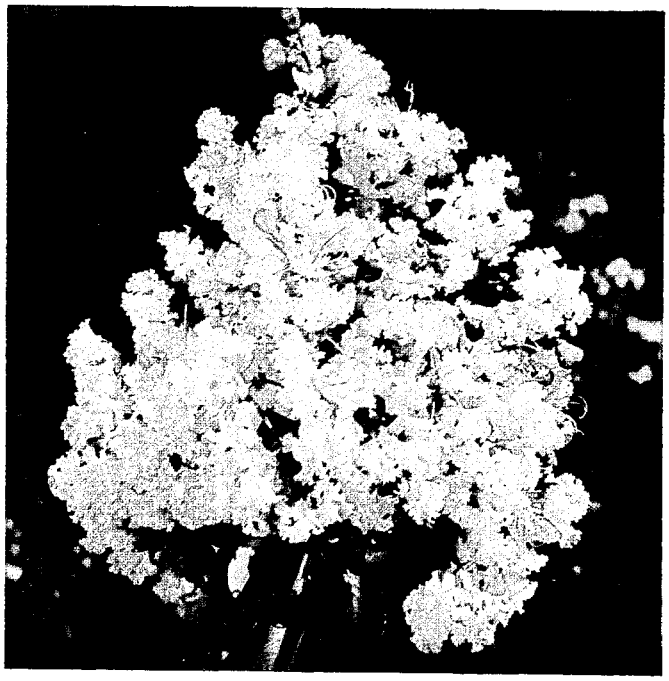
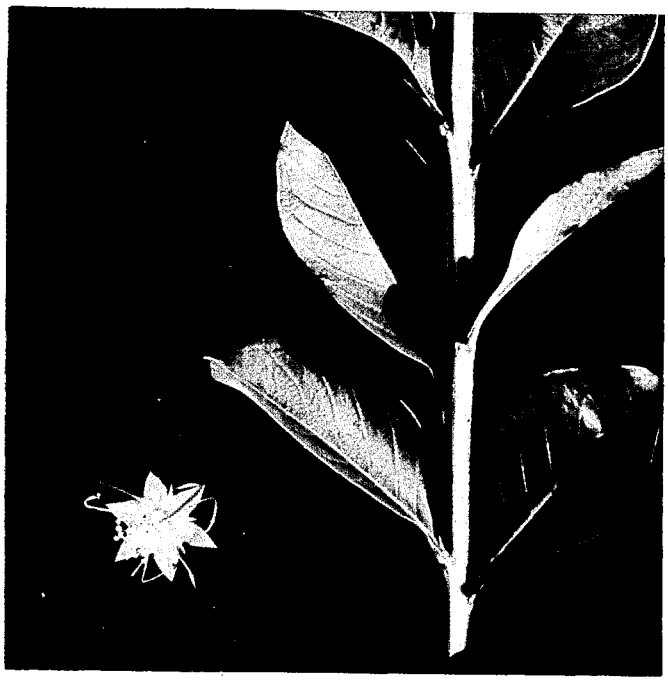

United States Patent Office

Plant Pat. 3,504
Patented Mar. 5, 1974

3,504
*LAGERSTROEMIA INDICA*

Jacques Desmartis, 15 Avenue Wilson,
Bergerac, France

Filed May 22, 1972, Ser. No. 255,871
Claims priority, application France, May 21, 1971, 7119390
Int. Cl. A01h *5/00*
U.S. Cl. Plt.—54 1 Claim

ABSTRACT OF THE DISCLOSURE

A *Lagerstroemia indica* variety (Indian lilac) having pink flowers, winter weather resistance to temperatures below —10° C., straight tree-like growth and uniform leaf and heavy uniform blossom distribution.

(1) FIELD OF THE INVENTION

The present invention relates to a new and distinctive variety of Indian lilac (*Lagerstroemia indica*) which has been asexually reproduced by me by rooting cuttings of seedlings, shrubs and other plants resulting from a definite effort to produce a lilac variety having a particularly aesthetic pale pink flower.

(2) BACKGROUND OF THE INVENTION

The parent strain of the new variety, *Lagerstroemia indica* or Indian lilac is believed to have been introduced into Europe in the middle of the 18th century from southern Asia. The plant received little acceptance because flowering was never certain or consistent and the coloration of the blossom was often dull and uninteresting. The plant was susceptible to many diseases and the variety was unusually sensitive to low temperatures, so that it was incapable of wintering severe climate and a freeze generally killed the plant. With this background I undertook to develop a new variety of *Lagerstroemia indica* without the aforedescribed disadvantages.

(3) DESCRIPTION OF THE DRAWING

In the drawing:

FIG. 1 is a color photograph of the flower of the plant according to the invention; and FIG. 2 is a color photograph of a stem portion and floret thereof.

(4) DESCRIPTION OF THE INVENTION

The new variety of *Lagerstroemia indica* or Indian lilac, according to the present invention is a hybridized and selected variety which traces back to the *Lagerstroemia indica* brought to Europe in the middle of the 18th century and is characterized by a unique pale pink blossom coloration, extraordinarily high degree of floral abundance with respect to blossoms, large uniform accumulation of blossoms, particularly pronounced floral definition and exceptional vigorous blossom-endurance and overall tree-like form.

(a) Origin of the variety according to the present invention

The *Lagerstroemia indica* variety having pale pink blossoms is apparently derived from an accidentally produced hybrid which was introduced into southern France subsequent to the introduction of the basic variety into Europe. The accidental hybrid was cultivated and repeated cross pollination eventually yielded two types which had a pronounced pale-pink coloration vastly superior to the parent in aesthetic appearance. Pollen from one of the pale-pink species was applied to 15 castrated blossoms of the other and the seed capsules were obtained from the pairings of the two selected general types. The seeds from these capsules were planted to obtain a first generation hybrid of which several members were retained or selected.

From these members by cross-pollination and grafting applicant was able to produce 22 distinctive strains having pink inflorescence. From these plants, five were selected using as a guide, the closeness of the reproduced plants to the parent plant. From this group, plants were selected which resisted cold most successfully to temperatures of —10° C. and eventually a particularly attractive plant was isolated and asexually reproduced by rooting cuttings thereof, to constitute the subject matter of the present application.

(b) General characteristics of the plant according to the invention

The hybridized pink *Lagerstroemia indica* of the present invention is characterized by a high abundance of blossoms and is thus particularly floriferous, grows into a tree-like straight tall plant, resists wintering well and is winter-resistant at a temperature of —10° to 15° C. In southwest of France it comes into blossoms between mid-July and the end of August and then may bloom again in autumn when the weather is cold. A leaf-cutting of the plant may easily be rooted in water or any conventional rooting medium so that asexual reproduction of the shrub is simple.

(c) Botanical characteristics class

Hybrid of *Lagerstroemia indica* differing from the parent variety by a pronounced pale-pink coloration of the blossoms, attractive distribution of the leaves and stem, tree-like upward-growth characteristics and an abundance of blossoms when grown outdoors.

Plant.—Straight uniform tree-like upward-growth reaching the height of 1.80 m. within four years of starting from a 3-year-old cutting in the southwest of France. At this stage the plant has as essentially square cross section stem with a circumference of 5 to 6 cm.

The flowers are graceful and laden with individual blossoms or inflorescences which are evenly distributed and hang outwardly due to their weight. They have a conical configuration (see FIG. 1 which is a color photograph of a flower clump characterizing the plant of the present invention), the flowers are thus particularly graceful and may hang outwardly due to their weight. The distribution is uniform and substantially symmetrical.

Stalk.—The stalk has a generally square cross-section and is covered by thin bark which changes yearly in patches (see FIG. 2 representing a typical view of the stalk and leaf insertion).

Leaves.—Inserted vertically, the leaves alternate and are grouped by twos on opposite sides of the stalk or stem (see FIG. 2). They are oval with their large part below and are generally acuminate. These leaves are always slightly concave and are from 30 to 60 mm. long and from 20 to 35 mm. wide.

The upper face of the limb is bright green and very smooth. The underside is light green and has a central vein and 6 to 9 secondary veins alternately and uniformly extending therefrom.

The base of the limb is very narrow and eared slightly. It is connected by a short petiole to a welt constituting the insertion on the branch. This branch is almost square in section due to the presence of two flutes at the base of each leaf.

Inflorescence.—The *Lagerstroemia indica* variety of the invention has a multiple-flowered panicle inflorescence which is originally of conical shape becoming generally square with time. This panicle is on the end of a branch and measures between 10 and 30 cm. long. The central stalk is curved due to the large number of florets. The panicle is formed of many smaller inflorescences distributed like the leaves.

The flower is formed of a smooth calyx or flower cup with six bright green integral sepals. The corolla is formed of six well-developed petals which are of uniform shape and quite wrinkled and crumpled. Each petal is gracefully carried by a pedicel almost as long as the limb of the petal and inserted between the lobes of the calix. This disposition gives the flower a characteristic star shape.

The color of the inflorescences is a pale pink which is almost transparent and corresponds to amaranthine pink (see the Horticultural Colour Chart of the Royal Horticultural Society, Ref. 530, Chart II).

The gynoecium is formed of six loculi surmounted by a filiform style on the terminal stigma.

The androecium is formed of very numerous stamens with well developed anthers. The fruit is an oval capsule having six valves.

The seeds are elongated and have a wing as long as their fertile portion.

Winter resistance.—The plant's resistance to freezing is good. In the winters of 1962–1963 and 1966–1967 which were very severe in the south of France, the original stock plants survived temperatures of —20° C. A stem of 5–6 mm. can survive temperatures of the order of —13° C. perfectly.

The *Lagerstroemia indica* of the invention thus has a graceful shape, bright green leaves, many compact panicles emerging from the leaves, the panicles being generally square and very pale pink resembling the amaranthine pink; the hybrid grows straight and has good resistance to freezing and endemic diseases. It flowers early and has branches which grow uniformly outwardly from the stalk.

I claim:

1. A new and distinctive variety of *Lagerstroemia indica* (Indian lilac) class, characterized as to novelty by its uniform and heavy abundance of pale-pink flowers, by its exceptionally vigorous growing habit and ability to winter at low temperatures, by the size, perfection and form of the bloom and unusual coloration, substantially as shown and described.

No References cited.

ROBERT E. BAGWILL, Primary Examiner